United States Patent [19]
Srivastava et al.

[11] Patent Number: 6,004,532
[45] Date of Patent: Dec. 21, 1999

[54] FORMULATION FOR TIN-$^{117M}$/ DIETHYLENETRIAMINEPENTAACETIC ACIDS

[75] Inventors: Suresh C. Srivastava, Setauket; George E. Meinken, Middle Island, both of N.Y.

[73] Assignee: Brookhaven Science Associates, Upton, N.Y.

[21] Appl. No.: 09/093,200

[22] Filed: Jun. 8, 1998

[51] Int. Cl.$^6$ ............................ A61K 51/00; A61M 36/14
[52] U.S. Cl. ...................... 424/1.65; 424/1.11; 424/1.37; 424/1.53; 534/10; 600/1; 600/3
[58] Field of Search .................... 424/1.11, 1.37, 424/1.65, 1.53, 9.1, 9.3, 9.4, 9.5, 9.6, 9.7; 534/7, 10–16; 606/1, 3

[56] References Cited

U.S. PATENT DOCUMENTS

| | | | |
|---|---|---|---|
| 4,533,541 | 8/1985 | Srivastava et al. | 424/1.1 |
| 5,853,695 | 12/1998 | Srivastava et al. | 424/1.65 |

OTHER PUBLICATIONS

Mathews•van Holde, Biochemistry (1990), "Tools of Biochemistry: Ways to Isolate and Purify Proteins and other Macromolecules", pp. 156–160.

Atkins, et al., "Biodistribution of Sn–117m(4+) DTPA for Palliative Therapy of Painful Osseous Metastases[1]", Radiology 1993; 186:279–283.

Atkins, et al., "Tin–117m(4+)–DTPA for Palliation of Pain from Osseous Metastases: A Pilot Study", J. Nucl. Med., 1995; 36:725–729.

Krishnamurthy, et al., "Tin–117m(4+) DTPA: Pharmacokinetics and Imaging Characteristics in Patients with Metastatic Bone Pain", J. Nucl. Med., vol. 38, No. 2, Feb. 1997.

V.J. Lewington, "Cancer Therapy Using Bone–Seeking Isotopes", Phys. Med. Biol., 41 (1998), 2027–2042.

Yano, et al., "Tin–117m: Production, Chemistry and Evaluation as a Bone–Scanning Agent", Int. J. of Applied Radiation and Isotopes, 1973, vol. 24, pp. 319–325.

Mausner, et al., "Improved Specific Activity of Reactor Produced $^{117m}$Sn with the Szilard–Chalmers Process", Appl. Radiat. Isot., vol. 43, N.009, pp. 1117–1122, 1992.

*Primary Examiner*—Jose' G. Dees
*Assistant Examiner*—Dameron Jones
*Attorney, Agent, or Firm*—Margaret C. Bogosian

[57] ABSTRACT

The invention provides improved formulations of $^{117m}$Sn ($Sn^{4+}$) DTPA which allow higher doses of $^{117m}$Sn ($Sn^{4+}$) to be administered than were previously possible. Methods for making pharmaceutical compositions comprising $^{117m}$Sn ($Sn^{4+}$) DTPA in which the amount of unchelated DTPA is minimized are disclosed along with methods of using the improved formlulations, both for palliation of bone pain associated with cancer and for treatment of osseous tumors.

22 Claims, No Drawings

FORMULATION FOR TIN-$^{117m}$/ DIETHYLENETRIAMINEPENTAACETIC ACIDS

This invention was made with Government support under contract number DE-AC02-98CH 10886, awarded by the U.S. Department of Energy. The Government has certain rights in the invention.

The present invention relates to the fields of pain management for cancer patients and cancer therapy. In particular, the present invention relates to treatment of bone pain resulting from cancer metastases and to treatment of osseous (bone) cancer using improved formulations of $^{117m}$Sn ($Sn^{4+}$) diethylenetriaminepentaacetic acid.

BACKGROUND OF THE INVENTION

Bone metastases are the most common cause of cancer pain, and primary bone cancers may also cause severe chronic pain. Approximately 75–80% of patients with prostate, breast, and lung cancer develop osseous metastases which cause bone pain during the late stages of their illness. Clinical management of cancer-related bone pain through palliation is necessary to improve the quality of life of terminal cancer patients.

A number of options are currently available for clinical management of bone pain. Nonsteroidal anti-inflammatory agents, opioids, hormones, and cytotoxic chemotherapy are used in the initial stages of bone metastasis, and external beam radiation can be applied locally when bone pain occurs at a single site. As the patient's skeletal tumor burden increases, pain can increase and become multifocal, tending to move from one site to another. Hemibody external beam radiation can afford rapid pain relief for disseminated skeletal tumors. However, such extensive exposure to radiation may affect noncancerous rapidly dividing tissues in the gastrointestinal tract or bone marrow, and morbidity may result from hemibody radiotherapy for bone pain palliation.

Radiation emitted by intravenously administered radionuclides may also be used to treat bone pain palliation. A number of bone-seeking radioisotopes have been studied for their ability to palliate bone pain. For example, $^{32}$P, which emits a 1.7 MeV β particle and has a half-life of 14.3 days, exhibits a 3- to 5-fold increase in uptake in bone around osseous metastases as compared to normal bone. The uptake of $^{32}$P into bone lesions can be increased by pretreatment with androgen, and patients thus treated frequently experienced pain relief within five to fourteen days of $^{32}$P orthophosphate administration, with response duration of two to four months. However, bone marrow receives a disproportionately high dose of $^{32}$P from the surrounding inorganic bone matrix and from the cellular component of the bone marrow space, resulting in myelosuppression as a side effect. Pancytopenia resulting from myelosuppression by $^{32}$P, though reversible, may necessitate transfusions. $^{32}$P orthophosphate is not currently used for palliation of metastatic bone pain.

$^{153}$Sm emits an 0.81 MeV β particle, with a half-life of 46.3 hours. The stable $^{153}$Sm ethylenediaminetetramethylenephosphonate (EDTMP) complex has received FDA approval. Patients report clinical benefit within two weeks of $^{153}$Sm-EDTMP treatment, frequently within 48 hours of treatment, and pain relief may last from four to forty weeks. Reversible myelosuppression also results from bone pain palliation treatment with $^{153}$Sm-EDTMP. In addition, at the applied therapeutic doses (35 to 210 mCi) large amounts of radioactivity can be excreted in the patient's urine, creating contamination risks and potentially causing radiation cystitis.

$^{186}$Re emits a 1.07 MeV β particle and a 137 keV, 9% abundance γ photon, having a half-life of 89.3 hours. $^{186}$Re forms a stable complex with hydroxyethylidine diphosphonate (HEDP) which rapidly accumulates in osteoblastic metastases. Symptom relief occurs for 40–65% of patients within two weeks, and frequently within 24–48 hours. $^{186}$Re-HEDP causes reversible myelosuppression, and therapeutic doses of $^{186}$Re-HEDP (30 to 70 mCi) also create contamination and radiation cystitis risks. Phase III clinical trials of $^{186}$Re-HEDP have been completed.

$^{89}$Sr emits a 1.46 MeV β particle and has a half-life of 50.5 days. The biological half-life of $^{89}$Sr exceeds 50 days in osteoblastic metastases, as compared to 14 days in normal bone. Bone pain relief occurs in 60 to 80% of patients, with onset two to four weeks after injection, though some patients may not experience relief for as much as ten weeks after treatment. The average duration of relief from $^{89}$Sr treatment is from three to six months. Treatment with $^{89}$Sr delays development of new bone pain in pre-existing but clinically silent metastases. Four weeks after therapy, $^{89}$Sr treatment typically causes a 30% decrease in platelet count which recovers slowly over 12 weeks. Toxicity from $^{89}$Sr treatment is cumulative, resulting from the total absorbed dose of radiation delivered to the bone marrow and from replacement of marrow by tumor as disease advances. In 1993, the FDA approved an adult dosage of 4 mCi of $^{89}$SrCl$_2$ for bone pain palliation.

Although pain relief is believed to occur independently from radiation-induced tumor cell killing, administration of bone pain-palliating doses of $^{153}$Sm and $^{186}$Re results in transient changes in levels of certain biochemical markers related to cancer progression. When administered with low doses of cisplatin, $^{89}$Sr also demonstrates reductions in tumor markers. This observation has led to the suggestion that administration of higher doses of these nuclides might result in a tumoricidal effect. However, no anti-tumor effect or improvement in survival has been demonstrated to result from administration of $^{153}$Sm, $^{186}$Re, or $^{89}$Sr, and the ability to increase dosages of these nuclides is limited by their myelosuppressive effects.

$^{117m}$Sn emits low energy conversion electrons (0.13 and 0.16 MeV) and a 159 keV γ photon, having a half-life of 14.0 days. $^{117m}$Sn ($Sn^{4+}$) diethylenetriaminepentaacetic acid (DTPA) exhibits higher bone uptake and retention than $^{32}$P orthophosphate, $^{153}$Sm-EDTMP, $^{186}$Re-HEDP, and $^{89}$SrCl$_2$. Because of this, therapeutic doses of $^{117m}$Sn ($Sn^{4+}$) DTPA are lower than those of $^{153}$Sm-EDTMP and $^{186}$Re-HEDP, resulting in less risk of contamination and radiation cystitis. The lower energies of the conversion electrons emitted by $^{117m}$Sn result in less radiation exposure to the bone marrow and fewer hematologic side effects than are observed with $^{153}$Sm-EDTMP, $^{186}$Re-HEDP, and $^{89}$SrCl$_2$. The γ photon emitted by $^{117}$Sn allows imaging and quantification of the isotope in normal and metastatic bone. $^{117m}$Sn($Sn^{4+}$) is particularly suitable for the dose escalation necessary to effect cell killing in osseous tumors, since the myeclosuppression which limits the benefits of the anti-tumor effects of $^{153}$Sm, $^{186}$Re, and $^{89}$Sr is not a limiting factor for $^{117m}$Sn ($Sn^{4+}$).

Atkins, et al., *Radiology* (1993) 186, 279–283, discloses biodistribution of low doses of $^{117m}$Sn ($Sn^{4+}$) DTPA administered to humans. Atkins, el al. (1995) *J. Nucl. Med.* 36, 725–729 reports a Phase II pilot study which demonstrates palliation of bone pain resulting from $^{117m}$Sn ($Sn^{4+}$) DTPA treatment. A Phase II study of $^{117m}$Sn ($Sn^{4+}$) DTPA as a bone pain palliation agent is reported in Krishnamurthy, et al. (1997) *J Nucl. Med.* 38, 230–237. A dose escalation study of 47 patients treated with $^{117m}$Sn (Sn$^{4+}$) DTPA for bone pain palliation is reported in Srivastava, et al. (1998) *Clin. Cancer Res.* 4, 61–68. All of the $^{117m}$Sn (Sn$^{4+}$) DTPA formulations used in these studies contained a 20-fold molar excess of DTPA over $^{117m}$Sn (Sn$^{4+}$) and an amount of CaCl$_2$ corresponding to 80% of the molar amount of DTPA. The CaCl$_2$ was administered with the $^{117m}$Sn (Sn$^{4+}$) DTPA to counteract any potential effect of uncomplexed DTPA on bone or blood calcium levels.

U.S. Pat. No. 4,533,541 discloses preparation of $^{117m}$Sn (Sn$^{4+}$) chelates capable of localizing to bone after intravenous injection, which were used for diagnostic purposes. The chelating agents disclosed in U.S. Pat. No. 4,553,541 include DTPA, which was formulated in significant molar excess (8–40-fold) over the concentration of $^{117m}$Sn (Sn$^{4+}$) (i.e., the concentration of total tin) in the radiopharmaceutical composition.

WO 95/29706 discloses $^{117m}$Sn (Sn$^{4+}$) DTPA compositions for bone pain palliation and bone cancer therapy which employ a molar excess of DTPA over $^{117m}$Sn (Sn$^{+4}$). WO 95/29706 demonstrates dose-dependent relief of bone pain in humans after administration of $^{117m}$Sn (Sn$^{4+}$) DTPA, with particular efficacy at doses of about 9 to about 25 mCi per 70 kg body weight. None of the $^{117m}$Sn (Sn$^{4+}$) DTPA compositions used in WO 95/29706 exhibited bone marrow toxicity, thus providing a significant advantage over the known agents. In a preferred embodiment, CaCl$_2$ was included with the $^{117m}$Sn (Sn$^{4+}$) DTPA compositions of WO 95/29706, to inhibit or retard possible hypocalcemic effects of unchelated tin chelating agents.

SUMMARY OF THE INVENTION

The improved formulations of $^{117m}$Sn (Sn$^{4+}$) DTPA and improved methods for making $^{117m}$Sn (Sn$^{4+}$) DTPA encompassed by the present invention minimize the amount of unchelated DTPA administered to the patient, thereby minimizing potential side effects caused by the presence of unchelated DTPA in the patient's body. The improved $^{117m}$Sn (Sn$^{4+}$) DTPA formulations of the invention allow lower specific activity $^{117m}$Sn (Sn$^{4+}$) to be used for bone pain palliation. The present invention also allows higher dosages of $^{117m}$Sn (Sn$^{4+}$) to be used for treatment of primary and metastatic osseous cancers than was previously possible. The improved $^{117m}$Sn (Sn$^{4+}$) DTPA formulations of the invention provide greater flexibility in manufacturing and dosage of the therapeutic agent.

In one embodiment, the invention provides a pharmaceutical composition comprising $^{117m}$Sn (Sn$^{4+}$) at a first molar concentration and DTPA at a second molar concentration, the second molar concentration being from about one to about seven times the first molar concentration.

In another embodiment, the invention provides a method of making a pharmaceutical composition of $^{117m}$Sn (Sn$^{4+}$) DTPA from a $^{117m}$Sn (Sn$^{4+}$) DTPA precursor composition, wherein the $^{117m}$Sn (Sn$^{4+}$) DTPA precursor composition is formed by the steps of dissolving metallic $^{117m}$Sn in a concentrated acid; diluting the dissolved $^{117m}$Sn to yield a solution of $^{117m}$Sn (Sn$^{2+}$) having a determinable molar concentration; adding DTPA at a molar concentration from about eight to about twenty times the molar concentration of $^{117m}$Sn (Sn$^{2+}$); allowing a $^{117m}$Sn (Sn$^{2+}$) DTPA complex to form; oxidizing the $^{117m}$Sn (Sn$^{2+}$) DTPA to form a precursor composition containing $^{117m}$Sn (Sn$^{4+}$) DTPA and uncomplexed DTPA. In the method of the invention, sufficient unchelated DTPA is removed from the $^{117m}$Sn (Sn$^{4+}$) DTPA precursor composition to yield a pharmaceutical composition comprising $^{117m}$Sn (Sn$^{4+}$) and DTPA at a molar ratio from about 1:1 to about 1:7.

In yet another embodiment, the invention provides a method of treating bone pain associated with cancer in a human comprising the step of administering to the human a bone pain palliating amount of a pharmaceutical composition comprising $^{117m}$Sn (Sn$^{4+}$) at a first molar concentration and DTPA at a second molar concentration, the second molar concentration being from about one to about seven times the first molar concentration.

The invention also provides a method of treating a primary or metastatic tumor in skeletal bone of a human comprising the step of administering to the human a therapeutically effective amount of a pharmaceutical composition comprising $^{117m}$Sn (Sn$^{4+}$) at a first molar concentration and DTPA at a second molar concentration, the second molar concentration being from about one to about seven times the first molar concentration.

DETAILED DESCRIPTION OF THE INVENTION

The patent and scientific literature referenced herein establish the knowledge available to those with skill in the art. The issued U.S. patents and allowed applications are hereby incorporated by reference.

The improved $^{117m}$Sn (Sn$^{4+}$) DTPA formulations of the present invention may be used in the therapeutic and diagnostic methods disclosed in WO 95/29706 and its parent, U.S. application Ser. No. 08/237,003, now abandoned; and in U.S. application Ser. No. 08/743,287.

$^{117m}$Sn may be produced for use in the present invention in any manner. For example, $^{117m}$Sn may be produced by the $^{116}$Sn(n,γ)$^{117m}$Sn reaction in a high flux reactor as described in U.S. Pat. No. 4,533,541. $^{117m}$Sn may also be produced using the inelastic neutron scattering reaction $^{117}$Sn(n,n'γ)$^{117m}$Sn in a high flux reactor as disclosed in WO 95/29706, U.S. application Ser. No. 08/237,003, and U.S. application Ser. No. 08/743,287. Alternatively, the $^{117}$Sn(n,n'γ)$^{117m}$Sn reaction may be performed in any reactor capable of producing neutrons having sufficient energy to effect the reaction, for example, in a low flux reactor although the $^{117m}$Sn produced in a low flux reactor will have a lower specific activity than $^{117m}$Sn produced in a high flux reactor.

Prior to the present invention, low specific activity $^{117m}$Sn (Sn$^{4+}$) DTPA was less desirable for use as a radiopharmaceutical than high specific activity $^{117m}$Sn (Sn$^{4+}$) DTPA, because more of the low specific activity composition would have to be administered to the patient to deliver the dose of radioactivity necessary to effect bone pain palliation or remediation of primary or metastatic osteosarcoma. The presence of high concentrations of unchelated DTPA in the low specific activity $^{117m}$Sn (Sn$^{4+}$) DTPA composition could limit the amount of the composition that could be administered without toxic effects such as hypocalcemia. Less of the high specific activity $^{117m}$Sn (Sn$^{4+}$) DTPA composition, and consequently less unchelated DTPA, would be required to administer the required dosage of radioactivity. Because the amount of unchelated DTPA is minimized in the pharmaceutical compositions of the present invention, lower specific activity $^{117m}$Sn (Sn$^{4+}$) may be employed, both for bone pain palliation and for treatment of osteosarcoma.

The ability to use low specific activity $^{117m}$Sn in the pharmaceutical compositions of the present invention provides greater flexibility in manufacturing for several reasons. First, there are a larger number of low flux reactors and cyclotrons than high flux reactors. Second, nuclear reactions other than the presently preferred $^{117}$Sn(n,n' γ)$^{117m}$Sn reaction may be employed to produce $^{117m}$Sn. Moreover, because less unchelated DTPA is present in the pharmaceutical compositions of the invention, high specific activity $^{117m}$Sn (Sn$^{4+}$) DTPA containing compositions will have a longer shelf life than is presently possible, since a larger number of half-life decays can occur prior to expiration of the product.

$^{117m}$Sn may be produced in any way for use in the present invention, for example using any of the methods discussed in Mausner, et al. (1992) *Appl. Radiat Isot.* 43, 1117–1122. As disclosed in WO 95/29706, enriched $^{117}$Sn may be obtained as an oxide or as the metal, for example, from Oak Ridge National Laboratory, Oak Ridge, Tenn. The former may be converted to the metal by reduction at 600° C. in a hydrogen flow for 2.5 hours. A target may be prepared by sealing 4 to 100 mg of the $^{117}$Sn metal in a quartz ampule. To produce $^{117m}$Sn, the target is irradiated in a high flux reactor for periods up to 4 weeks. When $^{117m}$Sn is produced in a low flux reactor, the $^{117}$Sn target may be irradiated for periods of more than four weeks. $^{117m}$Sn may also be produced in a cyclotron, for example, by the $^{nat}$Sb(p,an/a3n) $^{117m}$Sn reaction or by the $^{114}$Cd(a,n)$^{117m}$Sn reaction.

The $^{117m}$Sn produced as described above may be dissolved in a minimal amount of a concentrated acid such as hydrochloric acid and added to a ten to 45-fold molar excess (over the molar amount of $^{117m}$Sn (Sn$^{2+}$) in the solution) of an acid salt of DTPA having a pH of about 7. The solution may optionally be heated in a boiling water bath to facilitate complexation, thereby producing $^{117m}$Sn (Sn$^{2+}$) DTPA. If a heating step is performed, the $^{117m}$Sn (Sn$^{2+}$) DTPA solution is cooled. An oxidizing agent such as hydrogen peroxide is added to oxidize the $^{117m}$Sn (Sn$^{2+}$) to $^{117m}$Sn (Sn$^{4+}$), and oxidation is allowed to proceed for a suitable time, for example, for ten to fifteen minutes when hydrogen peroxide is employed. A slight molar excess of calcium chloride may optionally be added. The resulting solution may be diluted to produce a $^{117m}$Sn (Sn$^{4+}$) DTPA precursor composition. A significant amount of unchelated DTPA may be present in this precursor composition.

Unchelated DTPA may be removed from the $^{117m}$Sn (Sn$^{4+}$) DTPA precursor composition using any suitable means. For example, unchelated DTPA may be removed using osmotic means such as dialysis or using chromatographic means. Preferably, a chromatographic means is employed to remove unchelated DTPA from the $^{117m}$Sn (Sn$^{4+}$) DTPA precursor composition. More preferably, high performance liquid chromatographic means is employed to remove unchelated DTPA from the $^{117m}$Sn (Sn$^{4+}$) DTPA precursor composition. Most preferably, high performance liquid chromatographic means using an anion exchange resin is used to remove unchelated DTPA from $^{117m}$Sn (Sn$^{4+}$) DTPA precursor composition.

In accordance with the present invention, a sufficient amount of DTPA is removed from the $^{117m}$Sn (Sn$^{4+}$) DTPA precursor composition to produce a pharmaceutical composition comprising $^{117m}$Sn (Sn$^{4+}$) and DTPA at a molar concentration ratio from about one to about seven. That is, in the pharmaceutical composition of the invention, for each mole of $^{117m}$Sn (Sn$^{4+}$) (or total tin) there will be from about one to about seven moles of DTPA, either chelated to $^{117m}$Sn (Sn$^{4+}$) or in unchelated form. Preferably, the pharmaceutical composition of the invention will contain from about one to about seven moles of DTPA for each mole of $^{117m}$Sn (Sn$^{4+}$). More preferably, the pharmaceutical composition of the invention will contain from about one to about four moles of DTPA for each mole of $^{117m}$Sn (Sn$^{4+}$). Most preferably, the pharmaceutical composition of the invention will contain from about one to about 1.5 moles of DTPA for each mole of $^{117m}$Sn (Sn$^{4+}$).

The pharmaceutical composition of the invention may optionally include an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition may also contain stabilizers, preservatives, buffers, or other additives known to those of skill in the art. In accordance with the invention, the pharmaceutical composition comprising $^{117m}$Sn (Sn$^{4+}$) DTPA at the above-specified molar ratios will be in the form of a pyrogen-free, parenterally acceptable aqueous solution. The preparation of such parenterally acceptable solutions, having due regard to pH, isotonicity, stability, and the like, is within the skill of those in the art. The pharmaceutical composition may also optionally include a suitable calcium salt as a toxicity control agent, as described in WO 95/29706, U.S. application Ser. No. 08/237,003, and U.S. application Ser. No. 08/743,287.

In one embodiment, the pharmaceutical composition of the present invention contains $^{117m}$Sn(Sn$^{4+}$) having a specific activity from about 0.1 mCi/mg to about 80 Ci/mg. In another embodiment, the pharmaceutical composition of the present invention contains $^{117m}$Sn(Sn$^{4+}$) having a specific activity from about 2 mCi/mg to about 80 Ci/mg. In yet another embodiment, the pharmaceutical composition of the present invention contains $^{117m}$Sn(Sn$^{4+}$) having a specific activity from about 2 mCi/mg to about 20 mCi/mg.

In the method of treating bone pain associated with cancer of the invention, a bone pain palliating amount of the pharmaceutical composition described above is administered to a human patient in need of such treatment. As defined herein, a "bone pain palliating amount" means the amount of $^{117m}$Sn (Sn$^{4+}$) DTPA sufficient to show a meaningful reduction in bone pain as determined by objective means, for example, using the Keele pain scale (Keele, K. D. (1948) *Lancet* 2, 6–8) or the Karnofsky performance scale (Karnofsky, D. A. (1963) *Clin. Pharmacol. Ther.,* 709–712). It is contemplated that the administered dosage of the pharmaceutical composition for relief of bone pain will be from about 6 mCi $^{117m}$Sn (Sn$^{4+}$) to about 50 mCi $^{117m}$Sn (Sn$^{4+}$) per 70 kg body weight (i.e., a total dosage from about 4 mCi to about 130 mCi). Preferably, the administered dosage is from about 10 mCi $^{117m}$Sn (Sn$^{4+}$) to about 50 mCi $^{117m}$Sn (Sn$^{4+}$) per 70 kg body weight (a total dosage from about 7 mCi to about 130 mCi). More preferably, the administered dosage is from about 10 mCi $^{117m}$Sn (Sn$^{4+}$) to about 30 mCi $^{117m}$Sn (Sn$^{4+}$) per 70 kg body weight (a total dosage from about 7 mCi to about 80 mCi). Most preferably, the administered dosage is from about 12 mCi $^{117m}$Sn (Sn$^{4+}$) to about 25 mCi $^{117m}$Sn (Sn$^{4+}$) per 70 kg body weight (a total dosage from about 9 mCi to about 65 mCi). Ultimately, specific treatment regimens appropriate for individual patients will be determined by the attending physician, taking into account the nature and severity of the condition being treated, and the nature of the prior treatments which the patient has undergone.

In the method of treating a primary or metastatic tumor in skeletal bone of the invention, a therapeutically effective amount of the pharmaceutical composition of the invention is administered to a human patient in need of such treatment. As defined herein, a therapeutically effective amount means the total amount of each active component of the pharmaceutical composition that is sufficient to show a meaningful patient benefit, i.e., a reduction in the size of the primary or metastatic tumor or in the incidence of additional metastatic tumors. It is contemplated that the administered dosage of the pharmaceutical composition for treatment of osseous tumors will be from about 10 mCi $^{117m}$Sn (Sn$^{4+}$) to about 1000 mCi $^{117m}$Sn (Sn$^{4+}$) per 70 kg body weight (i.e., a total dosage from about 7 mCi to about 1600 mCi). Preferably, the administered dosage is from about 10 mCi $^{117m}$Sn (Sn$^{4+}$) to about 300 mCi $^{117m}$Sn (Sn$^{4+}$) per 70 kg body weight (a total dosage from about 7 mCi to about 500 mCi). More preferably, the administered dosage is from about 10 mCi $^{117m}$Sn (Sn$^{4+}$) to about 100 mCi $^{117m}$Sn (Sn$^{4+}$) per 70 kg body weight (a total dosage from about 7 mCi to about 150 mCi). Most preferably, the administered dosage is from about 12 mCi $^{117m}$Sn (Sn$^{4+}$) to about 25 mCi $^{117m}$Sn (Sn$^{4+}$) per 70 kg body weight (a total dosage from about 9 mCi to about 50 mCi). Ultimately, specific treatment regimens appropriate for individual patients will be determined by the attending physician, taking into account the nature and severity of the condition being treated, and the nature of the prior treatments which the patient has undergone.

In practicing the methods of the present invention, a bone pain palliating amount or a therapeutically effective amount of the pharmaceutical composition is administered to a human, preferably by intravenous injection.

The invention is further described in the examples set forth below, which are intended to illustrate the invention without limiting its scope.

EXAMPLE 1

Preparation of $^{117m}$Sn (Sn$^{4+}$) DTPA (1:1)

An ampule containing irradiated $^{117m}$Sn metal was crushed into a closed system and the metal dissolved in a minimum volume of hot, concentrated HCl. The dissolved $^{117m}$Sn (as Sn$^{2+}$) was then added to 20 mole equivalents of H$_5$DTPA pH adjusted to 7.0. Two mole equivalents of 30% H$_2$O$_2$ was added to the stirred $^{117m}$Sn DTPA to oxidize the $^{117m}$Sn (Sn$^{2+}$) DTPA to $^{117m}$Sn (Sn$^{4+}$) DTPA. After 10–15 minutes, an aqueous solution containing 1.6 mole equivalents of CaCl$_2$ was added to the stirred $^{117m}$Sn(Sn$^{4+}$)DTPA. The solution was diluted to an appropriate volume with water for injection and filtered through an 0.22 μm syringe filter to yield a solution having the following composition: 1.5 mg Sn/mL; 58 mg DTPA/mg Sn; 0.6 mg CaCl$_2$/mg Sn.

An 0.1 mL, aliquot of diluted $^{117m}$Sn (Sn$^{4+}$) DTPA solution containing 0.04 mg Sn and 2.55 mg DTPA was loaded onto a 7.5×75 mm Biogel TSK DEAE 5PW anion exchange column (catalog number 125-0661, Biorad, Richmond, Calif.). An inverted parabolic gradient of 0.05 M to 0.4 M phosphate buffer pH 4.5 was applied to the column, and the retention values indicated in Table I were observed:

TABLE 1

| Species | Retention Value |
| --- | --- |
| $^{117m}$Sn(Sn$^{4+}$)DTPA | 1 |
| $^{117m}$Sn(Sn$^{2+}$)DTPA | 4.2 |
| DTPA | 4.6 |

The $^{117m}$Sn (Sn$^{4+}$) DTPA eluting at retention value 1 had a molar ratio of DTPA to $^{117m}$Sn (Sn$^{4+}$) DTPA of 1:1.

The radiochemical purity of the HPLC purified $^{117m}$Sn (Sn$^{4+}$) DTPA was assayed and compared with that of HPLC purified material to which fourfold and sixfold molar excess DTPA was added. The radiochemical purity of unpurified material was also assayed. Aliquots were spotted on chromatographic paper strips, and were developed with a solution of 1 mg/ml DTPA, pH 5–6. $^{117m}$Sn (Sn$^{4+}$) DTPA moves with the solvent front, while unhydrolyzed or uncomplexed tin remains at the origin. Results are shown in Table 2.

TABLE 2

| $^{117m}$Sn(Sn$^{4+}$):DTPA | % at Origin | % at Solvent Front |
| --- | --- | --- |
| 1:1 | 4.9 | 90 |
| 1:4 | 0.84 | 98 |
| 1:6 | 0.25 | 99 |
| 1:20 | 0.64 | 97 |

Thus $^{117m}$Sn (Sn$^{4+}$) DTPA prepared in accordance with the invention has a radiochemical purity greater than or equal to 90%.

EXAMPLE 2

$^{117m}$Sn (Sn$^{4+}$) DTPA at Various Molar Ratios Biodistribution in Mice

DTPA was added to aliquots of $^{117m}$Sn (Sn$^{4+}$) DTPA (1:1) prepared in Example 1 to prepare solutions containing $^{117m}$Sn (Sn$^{4+}$) DTPA at $^{117m}$Sn (Sn$^{4+}$): DTPA molar concentration ratios of 1:4 and 1:6. $^{117m}$Sn (Sn$^{4+}$) DTPA at varying molar concentration ratios was injected intravenously into mice (five mice for each molar concentration ratio) and biodistribution at 24 hours was determined for the fresh preparation and also after storage of the material for seven days. Composition which had not been subjected to anion exchange, containing $^{117m}$Sn (Sn$^{4+}$) DTPA at a molar ratio of 1:20, was used as a control.

The biodistributions of $^{117m}$Sn (Sn$^{4+}$) DTPA at molar concentrations of 1:1; 1:4; and 1:6 did not differ in blood clearance or total whole body retained activity from that of $^{117m}$Sn (Sn$^{4+}$) DTPA (1:20). Uptake into various organs, in terms of percent injected dose per gram at 24 hours, is shown in Tables 3 and 4. Bone to tissue ratios for fresh and stored preparations of $^{117m}$Sn (Sn$^{4+}$) DTPA at the various molar ratios tested are shown in Table 5. From this data, it can be seen that $^{117m}$Sn (Sn$^{4+}$) DTPA prepared in accordance with the present invention has substantially the same biodistribution for at least seven days after preparation as $^{117m}$Sn (Sn$^{4+}$) DTPA prepared by previously known methods.

TABLE 3

Biodistribution of $^{117m}Sn(Sn^{4+})$DTPA (Fresh Preparations)
(% Dose/g)

| $^{117m}Sn(Sn^{4+})$:DTPA Molar ratio | Blood | Bone | Spleen | Stomach | Intestines |
|---|---|---|---|---|---|
| 1:1 | 0.062 ± 0.017 | 17.77 ± 0.72 | 0.34 ± 0.08 | 1.19 ± 0.97 | 0.09 ± 0.03 |
| 1:4 | 0.052 ± 0.016 | 18.60 ± 2.16 | 0.30 ± 0.12 | 0.74 ± 0.72 | 0.06 ± 0.01 |
| 1:6 | 0.058 ± 0.012 | 16.74 ± 1.29 | 0.24 ± 0.06 | 0.10 ± 0.09 | 0.06 ± 0.02 |
| 1:20 | 0.015 ± 0.004 | 17.43 ± 2.21 | 0.08 ± 0.02 | 0.04 ± 0.02 | 0.04 ± 0.00 |

| $^{117m}Sn(Sn^{4+})$:DTPA Molar ratio | Liver | Kidney | Heart | Lung | Muscle |
|---|---|---|---|---|---|
| 1:1 | 0.63 ± 0.16 | 1.42 ± 0.48 | 0.11 ± 0.04 | 0.32 ± 0.07 | 0.11 ± 0.07 |
| 1:4 | 0.56 ± 0.08 | 0.96 ± 0.17 | 0.09 ± 0.04 | 0.36 ± 0.12 | 0.13 ± 0.08 |
| 1:6 | 0.39 ± 0.05 | 0.86 ± 0.22 | 0.11 ± 0.10 | 0.25 ± 0.09 | 0.06 ± 0.05 |
| 1:20 | 0.29 ± 0.04 | 0.64 ± 0.09 | 0.05 ± 0.01 | 0.96 ± 0.01 | 0.08 ± 0.06 |

TABLE 4

Biodistribution of $^{117m}Sn(Sn^{4+})$DTPA (Stored Preparations)
(% Dose/g)

| $^{117m}Sn(Sn^{4+})$:DTPA Molar ratio | Blood | Bone | Spleen | Stomach | Intestines |
|---|---|---|---|---|---|
| 1:1 | 0.03 ± 0.01 | 16.31 ± 2.01 | 0.202 ± 0.034 | 0.103 ± 0.052 | 0.06 ± 0.02 |
| 1:4 | 0.029 ± 0.007 | 17.2 ± 3.49 | 0.388 ± 0.096 | 0.080 ± 0.025 | 0.057 ± 0.016 |
| 1:6 | 0.025 ± 0.011 | 17.3 ± 0.91 | 0.12 ± 0.05 | 0.063 ± 0.017 | 0.039 ± 0.008 |
| 1:20 | 0.015 ± 0.003 | 19.04 ± 1.13 | 0.070 ± 0.02 | 0.030 ± 0.013 | 0.032 ± 0.007 |

| $^{117m}Sn(Sn^{4+})$:DTPA Molar ratio | Liver | Kidney | Heart | Lung | Muscle |
|---|---|---|---|---|---|
| 1:1 | 0.356 ± 0.067 | 0.605 ± 0.040 | 0.110 ± 0.037 | 0.202 ± 0.046 | 0.093 ± 0.056 |
| 1:4 | 0.771 ± 0.25 | 0.647 ± 0.048 | 0.092 ± 0.026 | 1.16 ± 0.52 | 0.175 ± 0.077 |
| 1:6 | 0.299 ± 0.034 | 0.582 ± 0.044 | 0.091 ± 0.024 | 0.133 ± 0.039 | 0.089 ± 0.067 |
| 1:20 | 0.237 ± 0.029 | 0.48 ± 0.08 | 0.035 ± 0.007 | 0.084 ± 0.008 | 0.127 ± 0.127 |

TABLE 5

Biodistribution of $^{117m}Sn(Sn^{4+})$DTPA
(Bone to Tissue Ratios)

| $^{117m}Sn(Sn^{4+})$:DTPA Molar ratio | Blood | Spleen | Stomach | Intestines | Liver | Kidney | Heart | Lung | Muscle |
|---|---|---|---|---|---|---|---|---|---|
| 1:1 (fresh) | 291 | 52 | 15 | 193 | 28 | 12 | 163 | 56 | 165 |
| 1:1 (stored) | 544 | 81 | 160 | 272 | 46 | 27 | 148 | 81 | 175 |
| 1:4 (fresh) | 358 | 63 | 25 | 321 | 33 | 19 | 204 | 53 | 149 |
| 1:4 (stored) | 593 | 44 | 215 | 302 | 22 | 27 | 187 | 15 | 98 |
| 1:6 (fresh) | 289 | 71 | 163 | 266 | 43 | 19 | 152 | 67 | 284 |
| 1:6 (stored) | 705 | 145 | 275 | 445 | 58 | 30 | 191 | 130 | 195 |
| 1:20 (fresh) | 1169 | 215 | 447 | 405 | 60 | 27 | 387 | 182 | 208 |
| 1:20 (stored) | 1269 | 272 | 635 | 595 | 81 | 40 | 544 | 227 | 150 |

It should be understood that the foregoing disclosure emphasizes certain specific embodiments of the invention and that all modifications or equivalents thereto are within the spirit and scope of the invention as set forth in the appended claims.

We claim:

1. A pharmaceutical composition comprising $^{117m}Sn$ ($Sn^{4+}$) at a first molar concentration and DTPA at a second molar concentration, the second molar concentration being from about one to seven times the first molar concentration.

2. The composition of claim 1, wherein the second molar concentration is from one to about four times the first molar concentration.

3. The composition of claim 1, wherein the second molar concentration is from one to about 1.5 times the first molar concentration.

4. The composition of claim 1, wherein the $^{117m}Sn$ ($Sn^{4+}$) has a specific activity from about 0.1 mCi/mg to about 80 Ci/mg.

5. The composition of claim 1, wherein the $^{117m}Sn$ ($Sn^{4+}$) has a specific activity from about 2 mCi/mg to about 80 Ci/mg.

6. The composition of claim 1, wherein the $^{117m}$Sn (Sn$^{4+}$) has a specific activity from about 2 mCi/mg to about 20 mCi/mg.

7. A method of making a pharmaceutical composition of $^{117m}$Sn (Sn$^{4+}$) DTPA comprising the steps of:

a) dissolving metallic $^{117m}$Sn in a concentrated acid;

b) diluting the dissolved $^{117m}$Sn to yield a solution of $^{117m}$Sn (Sn$^{2+}$) having a determinable molar concentration;

c) adding DTPA at a molar concentration from about eight to about twenty times the molar concentration of $^{117m}$Sn (Sn$^{2+}$);

d) allowing a $^{117m}$Sn (Sn$^{2+}$) DTPA complex to form;

e) oxidizing the $^{117m}$Sn (Sn$^{2+}$) DTPA to form a composition containing $^{117m}$Sn (Sn$^{4+}$) DTPA and uncomplexed DTPA; and f) removing sufficient unchelated DTPA from the composition to yield a pharmaceutical composition comprising $^{117m}$Sn (Sn$^{4+}$) and DTPA at a molar concentration ratio from about 1:1 to 1:7.

8. The method of claim 7, wherein the uncomplexed DTPA is removed from the $^{117m}$Sn (Sn$^{4+}$) DTPA precursor composition by chromatography.

9. The method of claim 8, wherein the chromatography employs an anion exchange resin.

10. In the method of making a pharmaceutical composition of $^{117m}$Sn (Sn$^{4+}$) DTPA comprising the steps of:

i) dissolving metallic $^{117m}$Sn in a concentrated acid;

ii) diluting the dissolved $^{117m}$Sn to yield a solution of $^{117m}$Sn (Sn$^{2+}$) having a determinable molar concentration;

iii) adding DTPA at a molar concentration from about eight to about forty times the molar concentration of $^{117m}$Sn (Sn$^{2+}$);

iv) allowing a $^{117m}$Sn (Sn$^{2+}$) DTPA complex to form; and v) oxidizing the $^{117m}$Sn (Sn$^{2+}$) DTPA to form a composition containing $^{117m}$Sn (Sn$^{4+}$) DTPA and uncomplexed DTPA;

the improvement comprising the further step of:

removing sufficient unchelated DTPA from the composition to yield a pharmaceutical composition comprising $^{117m}$Sn (Sn$^{4+}$) and DTPA at a molar concentration ratio from about 1:1 to 1:7.

11. A method of treating bone pain associated with cancer in a human comprising the step of administering to the human a bone pain palliating amount of a pharmaceutical composition comprising $^{117m}$Sn (Sn$^{4+}$) at a first molar concentration and DTPA at a second molar concentration, the second molar concentration being from about one to seven times the first molar concentration.

12. The method of claim 11, wherein the second molar concentration is from one to about four times the first molar concentration.

13. The method of claim 11, wherein the second molar concentration is from one to about 1.5 times the first molar concentration.

14. The method of claim 11, wherein the $^{117m}$Sn (Sn$^{4+}$) has a specific activity from about 0.1 mCi/mg to about 80 Ci/mg.

15. The method of claim 11, wherein the $^{117m}$Sn (Sn$^{4+}$) has a specific activity from about 2 mCi/mg to about 80 Ci/mg.

16. The method of claim 11, wherein the $^{117m}$Sn (Sn$^{4+}$) has a specific activity from about 2 mCi/mg to about 20 mCi/mg.

17. A method of treating a primary or metastatic tumor in skeletal bone of a human comprising the step of administering to the human a therapeutically effective amount of a pharmaceutical composition comprising $^{117m}$Sn (Sn$^{4+}$) at a first molar concentration and DTPA at a second molar concentration, the second molar concentration being from about one to seven times the first molar concentration.

18. The method of claim 17, wherein the second molar concentration is from one to about four times the first molar concentration.

19. The method of claim 17, wherein the second molar concentration is from one to about 1.5 times the first molar concentration.

20. The method of claim 17, wherein the $^{117m}$Sn (Sn$^{4+}$) has a specific activity from about 0.1 mCi/mg to about 80 Ci/mg.

21. The method of claim 17, wherein the $^{117m}$Sn (Sn$^{4+}$) has a specific activity from about 2 mCi/mg to about 80 Ci/mg.

22. The method of claim 17, wherein the $^{117m}$Sn (Sn$^{4+}$) has a specific activity from about 2 mCi/mg to about 20 mCi/mg.

\* \* \* \* \*